(12) United States Patent
Underwood

(10) Patent No.: US 7,193,694 B2
(45) Date of Patent: Mar. 20, 2007

(54) METHOD FOR GRADING GEMSTONE CUT AND SYMMETRY

(76) Inventor: William Underwood, 611 W. Dickson St., Fayetteville, AR (US) 72701

(*) Notice: Subject to any disclaimer, the term of this patent is extended or adjusted under 35 U.S.C. 154(b) by 20 days.

(21) Appl. No.: 11/119,984

(22) Filed: May 2, 2005

(65) Prior Publication Data

US 2006/0244946 A1    Nov. 2, 2006

(51) Int. Cl.
*G01N 21/00* (2006.01)
(52) U.S. Cl. .................................................. 356/30
(58) Field of Classification Search ............... 356/30, 356/31
See application file for complete search history.

(56) References Cited

U.S. PATENT DOCUMENTS

| | | | |
|---|---|---|---|
| 3,740,142 A | 6/1973 | Takubo | |
| 3,858,979 A | 1/1975 | Elbe | |
| 3,947,120 A | 3/1976 | Bar-Issac et al. | |
| 4,460,211 A * | 7/1984 | Pomeroy | 294/99.2 |
| 4,508,449 A * | 4/1985 | Okazaki | 356/30 |
| 4,907,875 A * | 3/1990 | Bowley et al. | 356/30 |
| 5,424,830 A | 6/1995 | Andrychuk | |
| 6,239,867 B1 | 5/2001 | Aggarwal | |
| 6,567,156 B1 | 5/2003 | Kerner | |
| 6,813,007 B2 | 6/2003 | Lapa et al. | |
| 2005/0254037 A1* | 11/2005 | Haske | 356/30 |

* cited by examiner

*Primary Examiner*—Gregory J. Toatley
*Assistant Examiner*—Roy M. Punnoose
(74) *Attorney, Agent, or Firm*—Mark Murphey Henry; Nathan Price Chaney; Stephen Douglas Schrantz

(57) ABSTRACT

An apparatus and associated method for the direct and objective grading of the cut and symmetry of gemstones is provided. The apparatus comprises a laser, an integration sphere, and a gemstone holder, which together measure certain optical characteristics of the gemstone. Optionally, the gemstone holder mechanically rotates and the integration sphere connects to a data recorder such that a plurality of measurements may be recorded and analyzed. The associated method provides a method for interpretation of the data generated by the apparatus as the data relates to the cut quality and symmetry of the gemstone.

2 Claims, 2 Drawing Sheets

METHOD FOR GRADING GEMSTONE CUT AND SYMMETRY

CROSS REFERENCES

None.

GOVERNMENTAL RIGHTS

None.

BACKGROUND OF THE INVENTION

Objective gemstone grading has long been an elusive goal for gemstone dealers. Historically, diamonds in particular have been measured based on the "four C's" known as clarity, carat size, color, and cut. Of these four characteristics, gemologists consider cut to be the most important in determining the quality of a diamond. Since 1953, the Gemological Institute of America (the "GIA") has issued industry-standard reports on diamonds that are designed to objectively measure clarity, carat size, and color. However, there is no system or apparatus in the prior art that directly and objectively measures diamond cut grade without making a comparison to a theoretical model, and it is the primary objective of the present invention to provide such an apparatus.

Upon closer examination of cut, there are three characteristics that are directly related to cut known as brilliance, dispersion, and scintillation. These three characteristics are natural, observable consequences of the geometric proportions of the individual facets of the diamond and the spatial relationship thereof, i.e., these three characteristics are subjective measures of the objective intensity of the light exiting via the crown of the diamond due to internal reflection and/or refraction.

For over five hundred years gem cutters have experimented with the geometric shape of a cut diamond in a quest to maximize a diamond's visual appeal as to the qualities of brilliance, dispersion, and scintillation. Thus, the art of gem cutting seeks to maximize a cut gemstone's optical reflective properties. The evolution of gemstone cut types includes the point, table, old single, Mazarin, Peruzzi, and old European cuts. One skilled in the art will recognize that the cuts of the prior art have contained increasingly numerous facets that allow each new cut to optically outperform its predecessor.

The purpose of each facet cut into a gemstone is to reflect and/or refract light such that the light entering a gemstone exits from the gemstone's crown. A gemstone is almost always mounted in a setting such that the crown is the portion of the gemstone intended to make a stunning visual impact on a viewer, and such impact is maximized when all facets are cut to optimal proportions. The state of the art for diamond cut types is the "round brilliant cut", first set forth by Marcel Tolkowsky in 1919.

Tolkowsky's round brilliant cut dictates that the ideal diamond has 57 or 58 facets (depending on whether a culet is present) arranged in a pattern with fairly low tolerances for deviation. Tolkowsky's formulation contemplated how the aesthetic qualities that made diamonds more vibrant, brilliant, and desirable were a direct result of the amount of light internally reflected out from the diamond's crown. Some purported advancements in the art have been made since Tolkowsky published his findings, resulting in contemporary diamonds having longer lower girdle facets and narrower pavilion main facets. It is an objective of the present invention to compare light emission readings of cuts conforming to the Tolkowsky standard and cuts using the alleged improvements on the Tolkowsky model to finally determine which theoretically diamond model is indeed superior. That is, the inventor believes the present invention will identify a more optimal gemstone cut should one be possible.

To date, the entire state of the art of grading cut quality and symmetry relies on comparing an examined diamond with a theoretically optimal diamond such as Tolkowsky's. The inventor has discovered a direct, objective way to measure the quality of a diamond's cut without making any comparisons to a theoretically optimal diamond. The inventor's discovery removes indirect calculations and subjective determinations from the analysis of the brilliance, symmetry, and cut quality of a diamond. Accordingly, it is a primary objective of the present invention to provide direct, objective, and repeatable means for analyzing the light emission from, and thus the cut quality of a diamond.

The inventor has determined that the amount of light that both enters and exits through the crown of a diamond is the most objective measure of a diamond's cut because the exiting light determines brilliance, dispersion, and scintillation, which are the qualities that make a diamond desirable to a consumer. For instance, two diamonds that appear identical based on the historically known GIA reports can actually vary greatly as to cut quality because the GIA report grades only color, clarity, and carat size. However, it is cut quality that almost exclusively influences the way a diamond handles light. A diamond that reflects a large percentage of light from its crown by virtue of internal reflection will appear larger and more brilliant than an historically similar diamond with an imperfect cut, and as such will be worth far more. A diamond that allows light to pass out of the pavilion instead of reflecting out of the crown is said to leak. Because a leaky diamond transmits less light to the viewer, the diamond appears smaller. Thus, an objective of the present invention is to identify gemstones that are cut in such fashion as to maximize the amount of light reflected from the crown and to minimize leakage of light from the pavilion.

As demonstrated by the teachings of Tolkowsky and others, symmetry is the most important factor in the cut quality of a diamond. The less symmetrical a diamond's geometry, the more light leaks from the diamond's pavilion and the less light reaches the viewer. A perfectly symmetrical cut diamond (with consistent and proper angles between the crown and pavilion) refracts light such that no light entering the crown of the diamond escapes from the pavilion. Of course, imperfections in characteristics such as the angles between facets and facet size, depth, and straightness all can affect a diamond's symmetry. It is thus an object of the present invention to capture measurements of a gemstone's intensity in a 360° circumferential direction such that the symmetry of the gemstone can be analyzed to establish the quality of the cut.

Beginning in the 1970's, the state of the art in diamond cut grading was a projection grading machine that casts a shadow of a diamond onto a template depicting the theoretically optimal cut of a diamond. Although this manually operated method is still employed, it has several severe drawbacks that minimize reliability and reproducibility. The measurements of projection-type grading machines are each subjectively made by the human eye, and as such there is a wide margin of error when compared to measurements performed by an automated and calibrated machine. Further subjectivity is introduced for each gemstone because the profile view of the gemstone must be analyzed several times, e.g., the jeweler must analyze eight different profiles for a round brilliant cut gemstone that exhibits octagonal symmetry. For over thirty years, the industry has felt a need for an apparatus that could objectively and automatically measure the cut grade of a diamond, yet the standard of the art has still relied upon subjective quantification. Again, it is an objective of the present invention to provide an apparatus that directly and objectively measures the cut quality and symmetry of a diamond.

Other past attempts at objectively measuring a gemstone's cut grade failed due to reliance upon uncontrolled ambient light to measure a gemstone's output intensity. The main problem with using ambient light is the inability to control the intensity of the light used to make measurements. This problem is highlighted by the fact that when the carat size of a gemstone is large, its "collective" characteristics are likewise large, i.e., the gemstone is capable of collecting more light due to the increased surface area of a larger gemstone. Therefore, past measurement techniques that utilize ambient light do not accurately measure cut quality because carat size directly influences any measurements of the intensity of light emitted from the gemstone. As a larger gemstone collects more light, measurements of the intensity of reflection and emission with ambient light do not provide reliable, consistent, or objective grading.

Other devices in the industry purport to objectively grade the cut of diamonds. Disclosed in U.S. Pat. No. 3,740,142 (the "'142 patent") is an apparatus for discriminating and identifying gemstones comprising a lightproof enclosure, a light source, and photographic film for recording the light rays as cast upon the photographic film by the gemstone. The light source illuminates the gemstone surrounded by the lightproof enclosure for the amount of time required to properly expose the photographic film. As many exposures of film must be loaded, manually developed, and examined to obtain images of each profile view of the gemstone, the requirement of film in this apparatus is cumbersome and time-consuming. Further, as with virtually all other attempts to quantify the diamond cut, the objects of the '142 patent ultimately rely upon subjective visual inspection of a photograph as developed from the exposure to light passed through a gemstone. Variances in photograph development diminish the objectivity and reproducibility of this method, as there is no calibration setting on this apparatus.

Disclosed in U.S. Pat. No. 3,858,979 (the "'979 patent") is an apparatus that measures the intensity of light for a discrete portion of the three-dimensional spherical space around a gemstone. This apparatus purports to measure weight, color, angle of cut, and quality of cut from measured reflections. This apparatus measures weight based on a comparative scale, i.e., the larger the gemstone, the greater the measurements of intensity internally reflected by the gemstone. This observation implicates an open system wherein the intensity of light used to make measurements is not known. The approach taken by the '979 patent includes aiming parallel light rays at, and perpendicular to, the table of a gemstone. Measurements of the reflections are taken by spiraling a small mirror around the surface of an imaginary sphere with the gemstone at the sphere's center. Discrete portions of the internal reflections from the gemstone are captured by reflections off the small mirror to a device that outputs the logarithm of the intensity of the light. The purpose of observing discrete portions of the area surrounding the gemstone is to record the reflections in a true illustration dependent on angle. The '979 patent also provides an apparatus for photographically recording the reflections in a discrete and rotational fashion; again, the use of photographic analysis is inherently subjective and incapable of calibration. The '979 patent exhibits additional deficiencies, including that it utilizes an open system for its light source, it measures only a discrete portion of the light reflected by the gemstone, and it includes no means for analyzing symmetry. In contrast, the present invention takes an entire holistic approach to measuring cut. It is thus an object of the present invention to directly and objectively measure the entire intensity of light internally reflected from the crown of a gemstone in a closed system, which gives a full understanding of the light-handling ability of the gemstone.

An additional deficiency of the '979 patent is that the collective ability of a larger gemstone skews the result when ambient light is used for illumination of the gemstone. In response to criticism about ambient light, the inventors of U.S. Pat. No. 3,947,120 (the "'120 patent") used a laser as a light source. This purportedly allows objective measurements by creating patterns of spots on photographic material that identify unique internal flaws in a diamond. The use of a laser is preferred because the light from a laser is of a specific wavelength and the light's intensity may be more closely controlled. However, the objects of the '120 patent are still inherently subjective because the measurements rely upon visual inspection of the photograph produced by the apparatus, the apparatus has no photograph calibration mode, and the '120 patent provides no means to objectively grade the cut of a gemstone.

Disclosed in U.S. Pat. No. 5,424,830 (the "'830 patent") is an apparatus for quantifying the facet angles of a gemstone. The apparatus directs collimated light towards a facet of a gemstone and measures the angle of reflection with a scale, which is based on simple trigonometry, that is parallel to the collimated light beam. The '830 patent utilizes a rotating holder such that all like facets may be systematically yet individually measured without removing the gemstone from the holder. The '830 patent contemplates and teaches individual, manual measurements.

Disclosed in U.S. Pat. No. 6,239,867 B1 (the "'867 patent") is a method and associated apparatus for grading of gemstones that is somewhat similar in implementation to the '830 patent. However, the '867 apparatus imports additional light sources to create two-dimensional images of the sides, top, and bottom of a gemstone. Using the two-dimensional images, an external data processor calculates the external three-dimensional geometry of the gemstone. The cut analysis is based on a comparison of the gemstone's geometry to a theoretical model such as Tolkowsky's standard. The analysis taught by the '867 patent is unreliable in two respects. First, the data processing step involves calculating the three-dimensional shape from two-dimensional image data, so significant data loss occurs when storing the shape as a plurality of two-dimensional images and also when reverse-engineering two-dimensional images into three-dimensional shapes. Second, the cut grade itself is based upon a comparison to a theoretical model, and the system for making such a comparison is inherently subjective due to the human-provided parameters that define the comparison. In contrast, it is an object of the present invention to use data processing means to visually depict direct, objective measurements of the light-handling characteristics of a gemstone.

A device known as the Sarin machine (of which there are several models) was developed to grade the cut of diamonds using a laser, and U.S. Pat. No. 6,567,156 issued on that invention. A Sarin machine uses a laser to determine the external three-dimensional geometric shape of a diamond. The measurements taken by a Sarin machine are once again compared to the theoretically optimal proportions of a diamond and thereafter assigned a "cut grade" based on the comparison, which the software provided with the Sarin machine assigns. The Sarin machine assigns the best cuts a '0' grade and the worst cuts a '10' grade. A deficiency of the Sarin machine is that the cut grade it provides is based solely upon the external three-dimensional geometry of a diamond, i.e., it fails to consider the internal characteristics of the diamond in calculating the cut grade. Those familiar with the art will recognize that diamond cutters avoid an uncut diamond's internal flaws when shaping the cut diamond. Thus, the internal characteristics of a diamond are relevant to the diamond's cut quality. Additionally, the measurements taken by the Sarin machine may be entered into a general-purpose computer to create a three-dimensional visual model of the diamond. Again, the human element of selecting an algorithm to compare the actual diamond to the theoretical diamond involves subjective decisions such as which theoretical model is used to make the comparison and unrelated concerns such as algorithmic efficiency.

Disclosed in U.S. Pat. No. 6,813,007 (the "'007 patent") is an apparatus that uses a camera to capture two-dimensional images of light internally reflected by a gemstone. Reverse-engineering the two-dimensional mapping of the reflected light captured by the images forms a three-dimensional model. The '007 patent purports to objectively measure certain characteristics of a diamond, but the analysis requires several intermediary steps to arrive at a three-dimensional model. The '007 patent's approach is similar to the one taken by both the '867 patent and the Sarin machine and is deficient for the same reasons, i.e., subjective determinations inherent in comparing a gemstone to a theoretical model, the loss of data in mapping a three-dimensional object onto two-dimensional images, and the disconnect between the actual measurements taken and the final, indirect, subjective result.

The pervasive deficiency of the entire body of prior art lies in the fact that no apparatus or method previously described directly and objectively measures diamond cut grade. For instance, the Sarin machine takes external measurements of a diamond and compares the measurements to a theoretical diamond such as the Tolkowsky model. Further, the Sarin machine bases its cut grade on the three-dimensional exterior shape of the diamond, not the diamond's internal characteristics; such a comparison is inherently problematic because it fails to consider the consequences of internal flaws incumbent in every diamond. An object of the present invention is to perform direct objective measurements of light entering and exiting a gemstone such that all relevant characteristics, including carat size, color, and clarity, are considered when determining the overall cut grade. Thus, a further objective of the present invention is to provide an apparatus that directly and objectively measures the cut of a gemstone.

It is a further objective of the present invention to provide an objective grade for the cut of a gemstone using measurements based on laser light.

It is a further objective of the present invention to objectively grade the cut of a gemstone based on the amount of symmetry displayed by a graphical representation of the measurements made with the disclosed apparatus.

The apparatus in accordance with the present invention provides a reliable, calibrated, reproducible, direct, and objective numerical measurement of the previously subjective determination of the cut quality of a gemstone.

BRIEF SUMMARY OF THE INVENTION

An apparatus and associated method for determining the cut quality of a gemstone is provided in which the total intensity of light emitted from the gemstone is expressed as a percentage of the light aimed at the crown of the gemstone. The gemstone comprises a crown, pavilion, and girdle, with the crown further comprising a flat table and facets between the table and the girdle. The apparatus comprises a gemstone holder, a laser aimed at the gemstone holder such that the angle of incidence of the laser's beam to the table of the gemstone is substantially perpendicular, and an integration sphere that substantially surrounds the gemstone such that external light sources do not influence the measurements taken by the apparatus. An integration sphere, which is not necessarily spherical, is a device that measures the light intensity of a closed system; thus, the integration sphere according to the present invention measures the total intensity of light emitted by the gemstone. The gemstone holder is capable of being freely rotated about an axis that is substantially parallel to the laser beam and substantially perpendicular to the table of the gemstone. The gemstone holder is adjustable to allow for various sizes and cuts of gemstones and also contains means to prevent measurement by the integration sphere of light leaked from the pavilion of the gemstone.

Another aspect of the invention discloses a data recorder capable of recording measurements as transmitted from the integration sphere. The measurements may be plotted as a bar graph, which may graphically depict symmetry demonstrated by the gemstone. If the cut is more desirable, the curve describing the plotted intensity values will be smooth and regular. If the cut is irregular, the plotted intensity values will show choppy and irregular curves. The perfectly cut round, brilliant diamond will have values that exhibit eight (8) peaks and eight (8) troughs. As a further indicator of a high quality cut, the peaks will exhibit substantially equal intensity values, as will the corresponding troughs. The spacing between adjacent peaks and adjacent troughs should also be substantially equal. While various statistical analyses may be performed on the data set provided by the apparatus to determine overall symmetry of the gemstone, the graph of the plotted intensity values contemplates a visual that will convey a large amount of information, even to a lay customer.

These and other advantages will become apparent from the following detailed description which, when viewed in light of the accompanying drawings, disclose the embodiments of the present invention.

DETAILED DESCRIPTION OF THE INVENTION

The present invention provides a rapid, repeatable, direct, comprehensive, calibrated, and objective measurement of a heretofore subjective quality of a gemstone. The inventor believes that the primary use of his invention will be to objectively demonstrate the subtle differences between gemstones to more accurately establish value. The present invention provides a method for graphically depicting the symmetry and cut of a gemstone that can be easily compared with such a graphical or statistical depiction of another gemstone. The inventor believes that this apparatus and method will be useful for distinguishing between two gemstones that have substantially identical characteristics as described by reports from the GIA.

The typical first step in a retail setting for analyzing the worth of a gemstone, especially a diamond, is to refer to a GIA report that sets forth several objective characteristics such as color, clarity, and weight. By example, two diamonds were analyzed using the present apparatus; the two diamonds had 'E' color grades, weighed 1.00 and 1.01 carats, and had SI2 clarity.

The next step performed in the prior art, again by way of example using the two similar example diamonds, is to analyze the diamond's cut using an apparatus that compares the diamond's geometric dimensions to that of a theoretical model. The DiaMension™ from Sarin Technologies, Inc. is one such apparatus, and the DiaMension™ assigns a cut grade from 0–10, with 0 being the best based on three-dimensional profile, but not on optical performance. Despite the virtual identity of the two example diamonds with respect to the color, clarity, and carat weight, the DiaMension™ machine assigned widely disparate cut grades to the two example diamonds. However, the DiaMension™ does not purport to explain the difference in optical performance of the two example diamonds. The human observer can see the difference, as the first example diamond appears larger and brighter than the second example diamond. The present invention was developed to objectively and directly explain this difference, which can be detected with the naked eye but cannot be directly explained by any apparatus in the prior art.

The present invention comprises a rotatable holder for a gemstone, a laser, and an integration sphere. These three components will produce the desired intensity measurements alone; however, as the disclosure of the preferred embodiment below will demonstrate, mechanical means for taking a plurality of different measurements and electronic means for recording the measurements is much easier and more accurate than taking the measurements by hand.

Building the Apparatus

Figure 1:
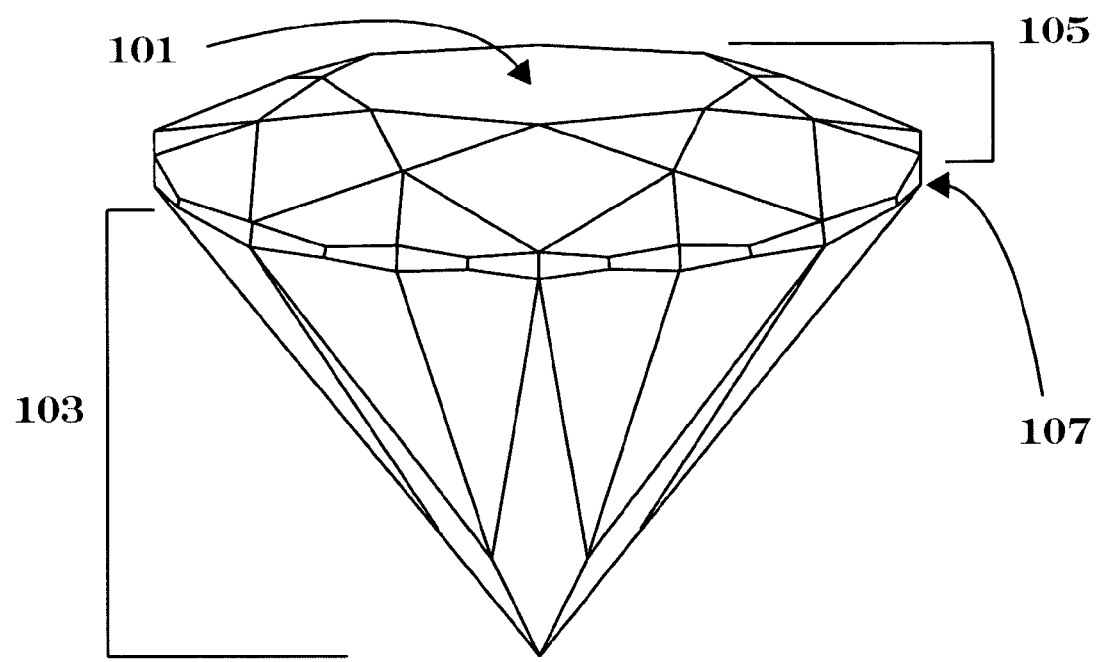
FIG. 1 is an illustration of the various parts of a round, brilliant cut gemstone 201, including the table 101, pavilion 103, crown 105, and girdle 107.
Figure 2:
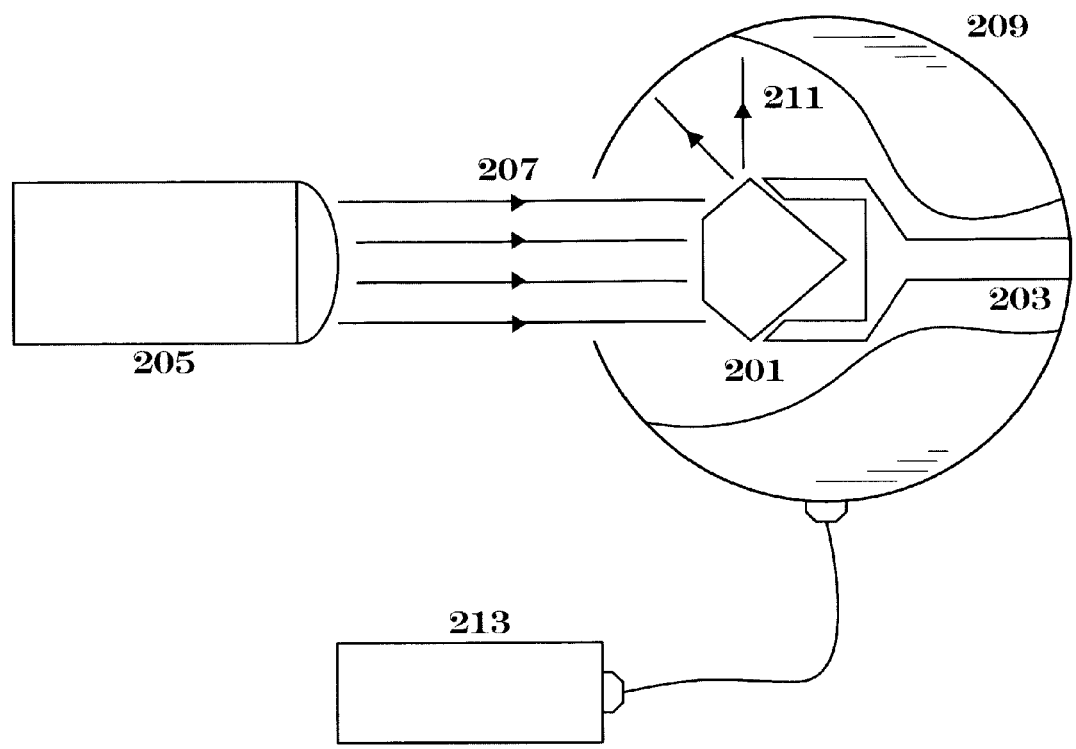
FIG. 2 is an illustration of the apparatus disclosed herein. Gemstone 201 is mounted in a gemstone holder 203 whereupon a laser 205 shines a laser beam 207. Laser beam 207 is aimed substantially perpendicular to table 101 of gemstone 201. An integration sphere 209 measures the overall intensity of the reflections 211 emitted from gemstone 201. A data recorder 213 records a plurality of the measurements taken by integration sphere 209.

Referring now to FIG. 2, the preferred embodiment of the present invention is practiced by coupling a laser 205 and an integration sphere 209. A gemstone holder 203 is mounted inside integration sphere 209 such that gemstone holder 203 immobilizes a gemstone 201 in a position where the gemstone's table 101 is substantially perpendicular to the laser beam 207 emitted from laser 205, and laser beam 207 enters the crown 105 of gemstone 201. Gemstone holder 203 serves the additional purpose of absorbing light that leaks from the pavilion 103 of gemstone 201 to prevent integration sphere 209 from measuring the leakage.

When laser 205 is turned on and gemstone 201 is properly secured by gemstone holder 203, integration sphere 209 will display a single measurement. Gemstone holder 203 further comprises means for rotating gemstone holder 203 precisely 360° about an axis that is substantially parallel to laser beam 207 in a set amount of time, and integration sphere 209 contains means to take a plurality of measurements of reflections 211 over the set amount of time that gemstone holder 203 will rotate through the entire 360°. Integration sphere 209 electronically transmits the numerical data to a data recorder 213, which records the numerical data. Data recorder 213 depicts the numerical data as, inter alia, a bar graph.

Analyzing Cut Quality

The method for analyzing the cut quality of gemstone 201 organizes the numerical data provided by integration sphere 209 according to average intensity of reflections 211. The average intensity correlates to the frequency with which individual measurements occur across the entire 360° of rotation, and both are utilized by computer software means to provide a single numerical beauty grade. For the highest cut grades, the average intensity should be very high in relation to the intensity of laser beam 207. Further, the frequency chart should be smooth, i.e., each recorded frequency should be present approximately the same number of times. Low average intensities and significant aberrations in the frequency chart, i.e., several large spikes or low troughs, are indicative of poorly cut gemstones. The preferred embodiment uses visual identification of aberrations on the frequency chart as well as statistical methods such as standard deviation to determine the effect and magnitude of any aberrations.

Analyzing Symmetry

The methods for analyzing the symmetry of gemstone 201 plot the intensity measurements made by integration sphere 209 and recorded by data recorder 213. The preferred embodiment uses at least one hundred eighty (180) unique measurements (one measurement for every 2° of rotation) to populate a bar graph. With such a plurality of measurements, the bar graph depicts a curve, and the shape of the curve is a direct representation of the symmetry of the gemstone 201.

Figure 3:
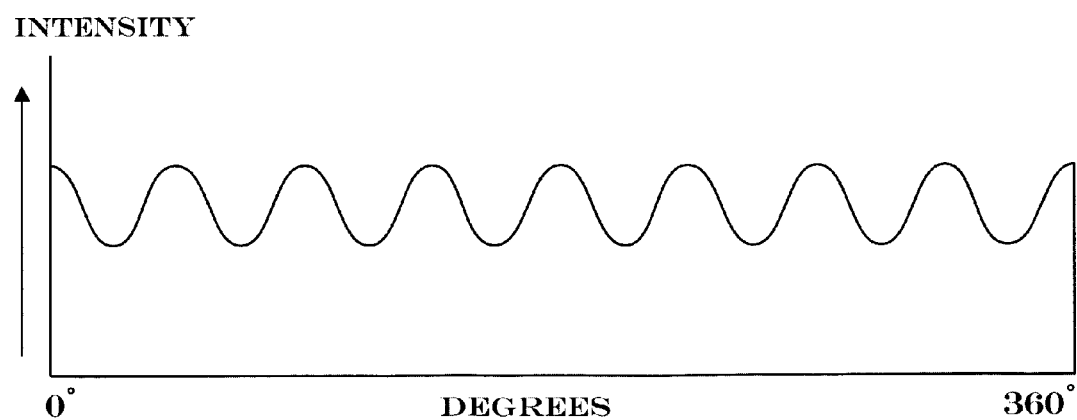
FIG. 3 is an illustration of an ideal bar graph representing the symmetry of gemstone 201 based on the intensity readings from integration sphere 209 as gemstone 201 is rotated about an axis that is substantially parallel to laser beam 207.

For a round brilliant cut diamond, presently considered the optimal cut of a gemstone, symmetry is represented by groups of eight (8) in the bar graph. The degree of symmetry is determined by either visual inspection of the bar graph or statistical methods such as standard deviation of each of the maximum and minimum points on the bar graph. The frequency chart described above also correlates to symmetry; the greater the number and deviation of aberrations, the more poorly a gemstone is cut. The bar graph of ideal symmetry resembles the graph of a sine wave as depicted by FIG. 3. Specifically, the eight (8) maximum intensity values on the graph are equal, as are the eight (8) minimum intensity values. The curve from each maximum to each minimum is smooth, and the distance between each of the adjoining maximum and minimums is equal.

Referring now to the two example diamonds that were virtually identical based on analyses under the prior art but not as to visual appearance, the first example diamond reflected a great majority of the laser beam 207, and the frequency with which each unique numerical intensity reading occurred was approximately the same. As to symmetry, the first example diamond exhibited eight (8) maximum and minimum points, each of which were evenly spaced from the adjoining maximum and minimum points. Each maximum and minimum intensity deviated little from the average maximum and minimum intensity. These measurements explain the reason the first example diamond appears larger and brighter than the second example diamond.

In contrast, the second example diamond scored lower on average intensity and also had several intensity readings well above and well below the average intensity reading, which skewed the frequency chart. Further, the second example diamond had eight (8) maximum and minimum points, but the deviation from the average maximum and minimum was far greater than the first example diamond. These deviations correlated with the aberrations on the frequency chart. The second example diamond also had significantly greater deviation in the distance between adjoining maximum and minimums, which is a characteristic of facets with dissimilar sizes, shapes, and angular relationships with neighboring facets. These measurements explain the reason the second example diamond appears smaller than the first example diamond.

While the inventor has described above what he believes to be the preferred embodiments of the present invention, persons having ordinary skill in the art will recognize that other and additional changes may be made in conformance with the spirit of the invention and the inventor intends to claim all such changes as may fall within the scope of the invention.

I claim:

1. A method for measuring the cut quality of a gemstone, comprising the following steps:
   a. calibrating a laser beam such that the intensity of the laser beam is known;
   b. mounting a gemstone in a gemstone holder such that the laser beam is directed toward the crown of the gemstone at an angle of incidence that is substantially perpendicular to the table of the gemstone; and
   c. measuring the intensity of reflected light from the gemstone with an integration sphere.

2. The method of claim 1, further comprising taking a plurality of measurements with the integration sphere as the gemstone is rotated about an axis that is substantially parallel to the laser beam.

* * * * *